US007553283B2

(12) United States Patent
Sandrin et al.

(10) Patent No.: US 7,553,283 B2
(45) Date of Patent: Jun. 30, 2009

(54) DEVICE AND METHOD FOR MEASURING ELASTICITY OF A HUMAN OR ANIMAL ORGAN AND FOR TWO-OR THREE-DIMENSIONAL REPRESENTATION THEREOF

(75) Inventors: Laurent Sandrin, L'Hay-les-Roses (FR); Jean-Michel Hasquenoph, Couilly-Pont-Aux-Dames (FR); Sylvain Yon, Paris (FR)

(73) Assignee: Echosens SA, Paris (FR)

( * ) Notice: Subject to any disclaimer, the term of this patent is extended or adjusted under 35 U.S.C. 154(b) by 49 days.

(21) Appl. No.: 10/526,417

(22) PCT Filed: Sep. 2, 2003

(86) PCT No.: PCT/FR03/02630

§ 371 (c)(1),
(2), (4) Date: May 13, 2005

(87) PCT Pub. No.: WO2004/021888

PCT Pub. Date: Mar. 18, 2004

(65) Prior Publication Data

US 2005/0251042 A1 Nov. 10, 2005

(30) Foreign Application Priority Data

Sep. 6, 2002 (FR) .................................... 02 11074

(51) Int. Cl.
*A61B 8/00* (2006.01)
(52) U.S. Cl. ........................................ 600/438; 600/443
(58) Field of Classification Search ................. 600/437, 600/443, 442, 449
See application file for complete search history.

(56) References Cited

U.S. PATENT DOCUMENTS 5,099,848 A 3/1992 Huang et al.

(Continued)

FOREIGN PATENT DOCUMENTS

FR 2 733 142 A 10/1996

(Continued)

OTHER PUBLICATIONS

Finks et al. Imaging method and device shear waves. Trans. David, Lawson. France: Sep. 21, 2000. WO/2000/055616.*

(Continued)

*Primary Examiner*—Eric F Winakur
*Assistant Examiner*—Helene Bor
(74) *Attorney, Agent, or Firm*—Stites & Harbison PLLC; Douglas E. Jackson; Stephen J. Weyer

(57) ABSTRACT

A device for measuring elasticity of a human or animal organ, or viscoelastic environments presenting an ultrasonic signal after ultrasonic illumination and consecutively establishing a representation in two or three dimensions of the elasticity, including at least one ultrasonic bar including a plurality of transducers, an excitor that generates and delivers a low-frequency, direct or indirect applied force, a receiver that acquires ultrasonic signals, a controller that commands and processes data, and a scanner that carries out scanning with the bar in one dimension (1D) or in two dimensions (2D) in two perpendicular directions, respectively, to obtain a representation of the measure of the elasticity in two (2D) or three dimensions (3D).

28 Claims, 3 Drawing Sheets

U.S. PATENT DOCUMENTS

| | | | | |
|---|---|---|---|---|
| 5,474,070 A | * | 12/1995 | Ophir et al. | 600/437 |
| 5,524,636 A | * | 6/1996 | Sarvazyan et al. | 600/587 |
| 5,810,731 A | * | 9/1998 | Sarvazyan et al. | 600/438 |
| 6,002,958 A | * | 12/1999 | Godik | 600/407 |
| 6,176,827 B1 | | 1/2001 | Cohen-Bacrie et al. | |
| 6,270,459 B1 | * | 8/2001 | Konofagou et al. | 600/449 |
| 6,277,074 B1 | | 8/2001 | Zhu et al. | |
| 6,371,912 B1 | * | 4/2002 | Nightingale et al. | 600/437 |
| 6,486,669 B1 | | 11/2002 | Sinkus et al. | |
| 6,490,470 B1 | * | 12/2002 | Kruger | 600/407 |
| 6,574,499 B1 | * | 6/2003 | Dines et al. | 600/427 |
| 6,758,815 B2 | * | 7/2004 | Bernardi | 600/437 |
| 6,770,033 B1 | * | 8/2004 | Fink et al. | 600/443 |
| 6,951,544 B2 | * | 10/2005 | Trahey et al. | 600/449 |
| 7,166,075 B2 | * | 1/2007 | Varghese et al. | 600/439 |
| 2002/0010398 A1 | * | 1/2002 | Bonnefous | 600/442 |
| 2003/0073905 A1 | * | 4/2003 | Bernardi | 600/449 |
| 2003/0171676 A1 | * | 9/2003 | Trahey et al. | 600/441 |
| 2004/0006273 A1 | * | 1/2004 | Kim et al. | 600/443 |
| 2005/0085728 A1 | * | 4/2005 | Fukuda | 600/449 |
| 2005/0107703 A1 | * | 5/2005 | Bullis | 600/442 |
| 2005/0165309 A1 | * | 7/2005 | Varghese et al. | 600/449 |

FOREIGN PATENT DOCUMENTS

| | | |
|---|---|---|
| WO | WO 00/55616 A | 9/2000 |
| WO | WO 01/76484 A | 10/2001 |
| WO | WO 02/35256 A | 5/2002 |

OTHER PUBLICATIONS

J. Bercoff et al., *Ultrafast compound imaging for 2d displacement vector measurements: application to transient elastography and color flow mapping*, 2001 IEEE Ultrasonics Symposium Proceedings, Atlanta, GA, Oct. 7-10, 2001, IEEE Ultrasonics Symposium Proceedings, New York, NY: IEEE, US, vol. 2 of 2, Oct. 7, 2001, pp. 1619-1622.

Sandrin, L. et al., "Shear Modulus Imaging with 2D Transient Elastography," IEEE Trans. Ultrason. Ferroelectr. Freq. Control, vol. 49(4), pp. 426-435 (2002).

Lu, J., "2D and 3D High Frame Rate Imaging with Limited Diffraction Beams," IEEE Trans. Ultrason. Ferroelectr. Freq. Contr., vol. 44(4), pp. 839-856 (1997).

Kasai, C. et al., "Real-Time Two-Dimensional Blood Flow Imaging Using an Autocorrelation Technique," IEEE Trans. Sonics Ultrason., vol. 32(3), pp. 458-464 (1985).

Konofagou, E.E. and Ophir, J., "A New Elastographic Method for Estimation and Imaging of Lateral Displacements, Lateral Strains, Corrected Axial Strains and Poisson's Ratios in Tissues," Ultrasound in Med. & Biol., vol. 24(8), pp. 1183-1199 (1998).

Tanter, M. et al., "Ultrafast Compound Imaging for 2D Motion Vector Estimation: Application to Transient Elastography," IEEE Trans. Ultrason. Ferroelectr. Freq. Control, vol. 49(10), pp. 1363-1374 (2002).

* cited by examiner

DEVICE AND METHOD FOR MEASURING ELASTICITY OF A HUMAN OR ANIMAL ORGAN AND FOR TWO-OR THREE-DIMENSIONAL REPRESENTATION THEREOF

RELATED APPLICATION

This is a §371 of International Application No. PCT/FR2003/002630, with an international filing date of Sep. 2, 2003 (WO 2004/021888, published Mar. 18, 2004), which is based on French Patent Application No. 02/11074, filed Sep. 6, 2002.

FIELD OF THE INVENTION

This invention relates to a device and a process for measuring the elasticity of a human or animal organ, or more generally all viscoelastic environments presenting an ultrasonic signal after ultrasonic illumination and the consecutive establishing of a two- or three-dimensional representation of the elasticity. It concerns in particular but not exclusively the measuring of the elasticity of a human breast. The significance of this technique is that the pathological nature of the tissues is frequently related to their elasticity.

BACKGROUND

French Patent Application Publication No. FR 2 733 142 discloses a device for measuring elasticity that realizes a measuring in 2 dimensions but is also suitable for realizing measurements in three dimensions. However, this device does not comprise a scanning means suitable for performing the scanning with the bar or bars in two perpendicular directions.

U.S. Pat. Nos. 6,176,827; 5,099,848; 6,277,074 and 5,474,070 and US Patent Application Publication No. 2002/0001098 disclose solutions for making only one measurement in two dimensions, at times with a fixed bar.

At the present time no ultrasonic devices for measuring the elasticity and allowing this measuring to be viewed in two or three dimensions are commercially available.

Furthermore, as concerns the measuring of elasticity in two dimensions, the article "Shear Modulus Imaging with 2D Transient Elastography" by L. Sandrin, M. Tanter, S. Catheline and M. Fink in Ultrason. Ferroelectr. Freq. Control, vol. 49 (4), pp. 426-435 (2002) is known and describes a technique for measuring elasticity and a representation in two dimensions of this measuring. The resolution of the inverse problem, that is to say, going back to the parameters that describe the viscoelastic environment to be measured, is imperfect here because the displacement is not known in the three spatial directions. In fact, according to the computational algorithms connected to the measurements carried out by the device presented in that article, the operators are obliged to formulate hypotheses to resolve the calculations of elasticity, but practice has demonstrated that these hypotheses are seldom justified.

WO 00/70362 discloses a system using magnetic resonance elastography (ERM), in which a viscoelastic zone (such as the human chest) is excited by mechanical waves. The subject matter of that invention is based on the hypothesis that the results of the measurements by ERM are solutions independent of the time of the partial differential equations precisely describing the behavior of mechanical waves in a viscoelastic material (including for longitudinal waves and in a reflecting environment). To this end the Young module contained in these equations can be calculated. In addition, it proposes using (in a predominant manner) longitudinal waves, that are capable of penetrating into the human chest, which is not the case for transversal waves. In that device, obtaining the elasticity map requires much time. Furthermore, the cost of implementing that device is very high.

French Patent Application Publication No. FR 2 791 136 discloses an imaging process for observing the propagation of an impulsive wave of low-frequency shearing at the same time in a multitude of points of a viscoelastic diffusing environment. To this end ultrasonic compression waves are emitted at an ultrarapid cadence that allows the obtention of a succession of images of the environment. Then, the images obtained are processed in non-real time by intercorrelation to determine at each point of each image the movements of the environment during the propagation of the shearing wave.

That invention is not satisfactory because it requires envisaging two hypotheses: the second derivative of the displacement is considered to be zero in the direction orthogonal to the plane, and the environment is assumed to be perfectly incompressible.

SUMMARY OF THE INVENTION

This invention relates to a device for measuring elasticity of a human or animal organ, or viscoelastic environments presenting an ultrasonic signal after ultrasonic illumination and consecutively establishing a representation in two or three dimensions of the elasticity, including at least one ultrasonic bar including a plurality of transducers, an excitor that generates and delivers a low-frequency, direct or indirect applied force, a receiver that acquires ultrasonic signals, a controller that commands and processes data, and a scanner that carries out scanning with the bar in one dimension (1D) or in two dimensions (2D) in two perpendicular directions, respectively, to obtain a representation of the measure of the elasticity in two (2D) or three dimensions (3D).

This invention also relates to a process for measuring elasticity of a human or animal organ, or viscoelastic environments presenting an ultrasonic signal after ultrasonic illumination and consecutively establishing a representation in two or three dimensions of the elasticity, including generating a low-frequency applied force or signal with an ultrasonic bar and acquiring ultrasonic signals, displacing the bar with a scanner in two perpendicular directions, generating ultrasonic images, calculating tissular speeds, and inverting the data by recovering parameters describing the viscoelastic environment.

BRIEF DESCRIPTION OF THE DRAWINGS

The invention will be described in the following by way of non-limiting example with reference made to the attached drawings.

DETAILED DESCRIPTION

Figure 1:
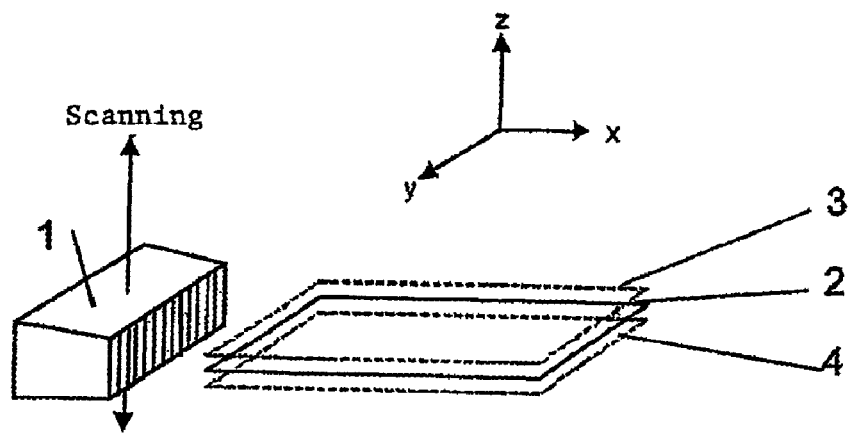
FIG. 1 is a schematic diagram showing the displacement of an echographic bar of the device of the invention provided with a simple mechanical scanning means.

This invention remedies disadvantages of the systems of the prior art. It provides a device for measuring the elasticity of a human or animal organ, in particular of a breast, or more generally all viscoelastic environments presenting an ultrasonic signal after ultrasonic illumination and the consecutive establishing of a representation in two or three dimensions of the elasticity, comprising at least one ultrasonic bar comprising a plurality of transducers or the like, an excitation means suitable for generating and delivering a low-frequency, direct or indirect applied force, a means for acquiring ultrasonic signals, a means for commanding and processing data such as a computer, and a scanning means suitable for carrying out a scanning with the above-mentioned bar in one dimension (1D) or in two dimensions (2D) in two perpendicular directions, respectively obtaining in this manner a representation of the measure of the elasticity in two (2D) or three dimensions (3D).

By means of these particularities the invention provides a device allowing the obtention of a mapping of the elasticity of the environment to be measured in two or three dimensions by virtue of a system that is relatively simple and inexpensive in comparison to existing solutions.

The ultrasonic bar advantageously comprises a plurality of transducers for acquiring ultrasonic signals.

According to one aspect of the invention the excitation means comprises a mechanical vibration that can be transversal, longitudinal or more generally a mixture of both. The excitation means can advantageously comprise one or several hyperthermal transducers because the elevation of the temperature produces displacements on the ultrasonic images either with the transducer(s) used for acquiring ultrasonic signals or one or several transducers arranged around the viscoelastic environment. In the same manner, the excitation means can also comprise internal movements of the human or animal body such as, e.g., the beating of the heart.

According to another aspect of the invention the excitation means comprises a remote palpation using the pressure of radiation either with the transducer(s) used for acquiring ultrasonic signals or one or several transducers arranged around the viscoelastic environment.

The device of the invention is advantageously controlled by at least one control means, e.g., a computer, a microcomputer or a central unit.

The ultrasonic bar is advantageously a 1.5 D bar or a wye transducer allowing a focusing at a plurality of different points of elevation. In this instance the scanning is realized by ultrasonic focalization. A "1.5 D bar," as it is called in the art, is a bar that is suitable not only for focusing along a plane but also in elevation relative to the plane, in the example along the horizontal plane parallel to the preceding one and slightly offset.

To facilitate the comprehension of the invention it is also noted, that an echographic bar with 0 D emits according to a linear dimension x, that a 1D bar emits according to a two-dimensional plane x, y and finally that a 2D bar customarily constituted of a multitude of ultrasonic transducers with a square shape distributed along a 2D matrix permits the emission of ultrasound in a volume according to the three dimensions x, y and z.

According to one aspect of the invention the space between the ultrasonic bar and the above-mentioned viscoelastic environment is constituted at least in part of water or any other element suitable for assuring the free passage of ultrasonic waves.

The unit constituted of the ultrasonic transducers and their on-board electronic components is advantageously connected to the command and processing means by a very high-speed digital connection, e.g., of the LVDS type.

According to one aspect of the invention the device in accordance with the invention comprises two ultrasonic bars. According to another aspect, the two bars are immersed in a hermetic container filled with a liquid, e.g., water. The hermetic container is advantageously connected to a rotation means suitable for rotating the container. According to another aspect of the invention the hermetic container can comprise a plurality of orifices into which a mechanical vibrator and/or an ultrasonic transducer is/are introduced. The orifices on or in the hermetic box are advantageously situated at 90° (degrees) from each other or the one from the other.

According to yet another aspect of the invention the device in accordance with the invention comprises three bars suitable for measuring the tissular speeds along directions y, x and z.

The invention also relates to a process for measuring the elasticity of a human or animal organ, in particular a breast, or more generally all viscoelastic environments presenting an ultrasonic signal after ultrasonic illumination and the consecutive establishing of a representation in two or three dimensions of the elasticity, comprising at least one ultrasonic bar or the like, excitation means suitable for generating low-frequency displacements, means for acquiring ultrasonic signals, means for commanding and processing data such as a computer, scanning means suitable for carrying out a scanning with the above-mentioned bar in one dimension (1D) or in two dimensions (2D), respectively obtaining in this manner a representation of the measure of the elasticity in two (2D) or three dimensions (3D), comprising the following stages:

generation of a low-frequency applied force or signal and the acquisition of ultrasonic signals, displacement of the bar due to the scanning means in two perpendicular directions, calculation of the ultrasonic images, calculation of the tissular speeds, and inversion of the data comprising recovering the parameters describing this viscoelastic environment.

The displacement stage of the bar is advantageously repeated as many times as necessary to acquire all the ultrasonic data before passing to the stage of calculating the ultrasonic images.

It should be noted that the stage of acquiring ultrasonic data also permits the acquisition of the data necessary for obtaining a classic ultrasonic image, that is to say, using a classic beamforming. In fact, the image or images obtained in this manner constitute information pertinent to 2D or 3D concerning the morphology of the organ studied, which information is fully complementary with the parameter of elasticity.

The second derivatives of the longitudinal component of this speed along the three orthogonal directions in space can advantageously be measured during the course of the stage of calculating tissular speeds.

In the same manner, during the course of the stage of calculating tissular speeds the spatial derivatives of the three components in the three spatial directions of this speed can be measured.

Turning to the drawings, the attached figures do not represent all conceivable aspects of the device. The device comprises the usual elements for realizing measurements of the elasticity of a human or animal organ, that is to say, especially by means of an ultrasonic bar or probe comprising a plurality of transducers, electronic equipment suitable for assuring the acquisition of ultrasonic signals, control and processing means of the data such as a computer or the like an excitation means suitable for producing low-frequency displacements.

The invention relates to the use of a mechanical scanning means that assures the scanning of the above-mentioned ultrasonic bar. This allows, by means of the process of the invention, parameters to be measured that are not accessible via the devices of the prior art, in particular the prior art described in FR 2 791 136. The parameters obtained in this manner are the second derivative of the displacement along the elevation, that is to say, the direction perpendicular to the plane of the image, and the two lacking components of the displacement vector.

The invention will be illustrated by reference to a breast or any other organ that is ideally static as a human or animal organ to constitute the object of the measuring of elasticity with the device and the process in accordance with the invention on the condition, of course, that an ultrasonic signal is presented after it was illuminated with the aid of ultrasonic signals. However, in the case in which the internal movements of the body cannot constitute a low-frequency applied force that can be used for the process, it is preferable that the organ is immobile in order not to disturb the measuring.

The process of the invention realizes the following steps in the following chronological order:

1. the generation of a low-frequency applied force or signal,
2. the acquisition of ultrasonic data,
3. the displacement of the bar by the scanning means,
4. the calculation of the ultrasonic images,
5. the calculation of the tissular speeds, also called displacement between successive images,
6. possible calculation of the tissular deformation speeds, and
7. inversion of the data, which allows the recovery of the parameters of the measured environment.

It should be noted that the calculating steps, that is, steps 4 to 6, can begin when the ultrasonic bar scans the viscoelastic environment, that is, that these steps ideally take place during displacement of the bar.

During the course of the step of generating the low-frequency applied force or signal a low-frequency signal is transmitted by means of excitation preferably immediately after the beginning of the ultrasonic acquisitions. This signal has a frequency f comprised between 5 Hz and 1000 Hz. The low-frequency vibration entrains the propagation in the tissues of the viscoelastic environment of low-frequency elastic waves whose propagation is a function of the elasticity of the environment.

The various means that can be used to bring about low-frequency displacements can comprise a mechanical vibration realized by a vibrator that can be in particular one or several vibrating plates 20, piston(s) and/or bar(s). In the same manner, the excitation means suitable for generating a shearing wave can comprise a remote palpation using the pressure of radiation either with the transducer(s) used for the acquisition of the ultrasonic signals or one or several transducers arranged around the object to be imaged.

During the step of acquiring the ultrasonic data, N ultrasonic acquisitions are realized at a cadence of 1/T typically comprised between 100 Hz and 100,000 Hz. The acquisition of the ultrasonic data takes place while emitting a short ultrasonic impulse with the ultrasonic transducers which impulse is reflected by the particles contained in the environment. The ultrasonic signal, called speckle, is recorded by the same ultrasonic transducers over a duration that can vary between one μs and 10 ms. This operation is repeated N times at the cadence 1/T.

Then the stage of the displacement of the echographic or ultrasonic bar takes place. At that stage, scanning comprises shifting the bar in three different manners as a function of the number and the type of ultrasonic bar used.

Thus, the device in accordance with the invention can be equipped in particular with:
 a single ultrasonic, unidirectional bar 1,
 two ultrasonic bars 5, 6 or one bar shifted along two axes,
 an ultrasonic bar 9 which is advantageously a 1.5 D type ultrasonic bar.

In the case of a single ultrasonic, unidirectional bar 1, represented in FIG. 1, echographic bar 1 is moved by a distance comprised between 10 μm and 10 mm. At least one scan in one direction is carried out. For example, a scan is made in direction z, constituted by plane 2 while moving from Δz, constituted in the figure by the two planes 3, 4.

Figure 2:
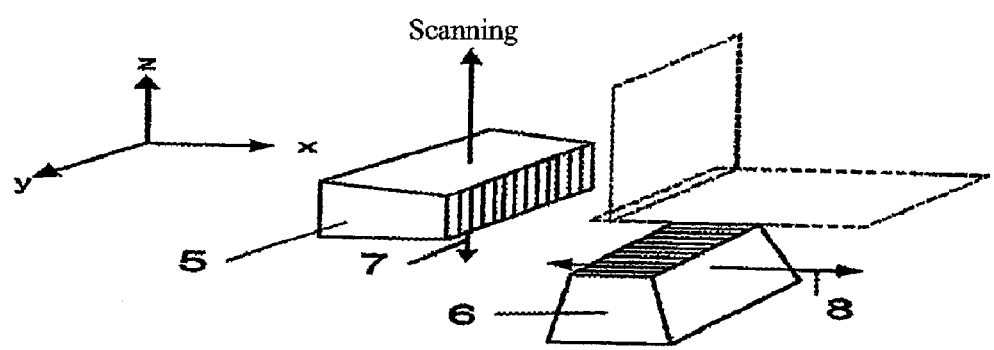
FIG. 2 is a schematic diagram showing the displacement of an echographic bar of the device of the invention provided with a double mechanical scanning means.

In the case of two ultrasonic bars 5, 6 represented in FIG. 2 or equivalent to one bar moved in two axes 7, 8, two bars 5, 6 are used (or one successively). This scanning allows all the components of the tissular speed vector to be accessed.

Figure 3:
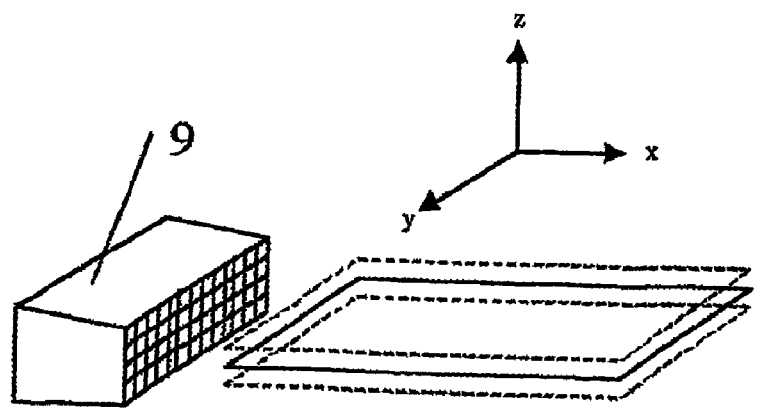
FIG. 3 is a schematic diagram showing the functioning of a 1.5 D bar of the device of the invention provided with a means for scanning by ultrasonic focalization in elevation.
Figure 4:
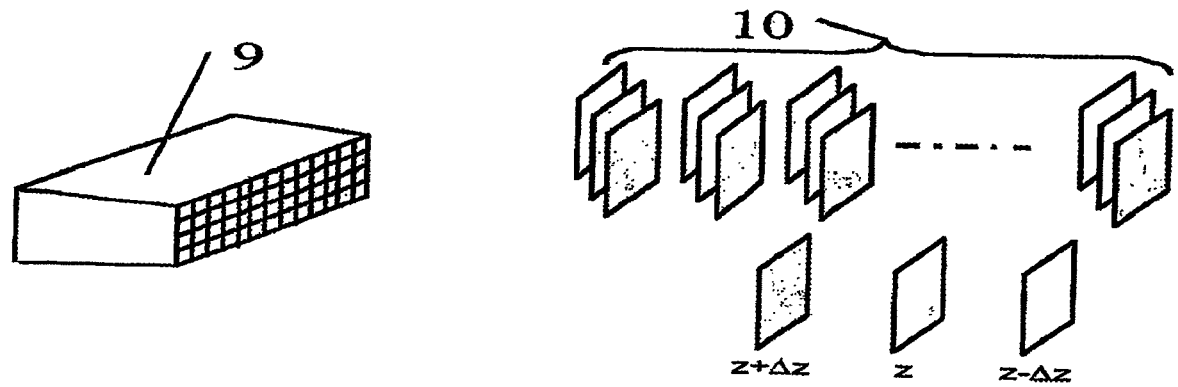
FIG. 4 is a schematic diagram showing the device of the invention provided with a 1.5 or 1.75 D bar suitable for focusing in elevation.

In the case of an ultrasonic bar 9 is advantageously a 1.5 D type, represented in FIG. 3, a mechanical scanning is avoided and the result is the same with a wye transducer. These two elements allow a focalizing in three different points of elevation. In the case of a 1.5 D bar the shift along z is obtained by modifying the laws of focalization in such a manner as to change the elevation of the image plane.

During the course of the step of calculating the ultrasonic images these images are constructed using an algorithm of summation-delay as described in French Patent Application Publication No. FR 2 791 136 cited above or using other types of rapid beamforming such as, e.g., the technique in space of spatial frequencies (see the article of J. Lu, "2D and 3D High Frame Rate Imaging with Limited Diffraction Beams", IEEE Trans. Ultrason. Ferroelectr. Freq. Contr., vol. 44, No. 4, 1997).

During the step of calculating the tissular speeds, also called "displacement between successive images," the tissular speeds or displacements between two successive but not necessarily consecutive ultrasonic shots are measured by intercorrelation, described in French Patent Application Publication No. FR 2 791 136 by Doppler, or by autocorrelation, described in particular in the article of C. Kasai, K. Namekawa, A. Koyano and R. Omoto, "Real-Time Two-Dimensional Blood Flow Imaging Using an Autocorrelation Technique", IEEE Trans. Sonics Ultrason., vol. 35, pp. 458-464 (1985), and more generally by any other technique for measuring displacements.

When using a simple mechanical scanning shown in FIG. 1, at least the component along x of tissular speed $V_x$ is accessed at each point of the environment situated in the imaged zone. When using an algorithm of the type described in the articles of E. E. Konofagou, J. Ophir, "A New Elastographic Method for Estimation and Imaging of Lateral Displacements, Lateral Strains, Corrected Axial Strains and Poisson's Ratios in Tissues", Ultrasound in Med. & Biol. 24, No. 8, pp. 1183-1199 (1998), and M. Tanter, J. Bercoff, L. Sandrin, M. Fink, "Ultrafast Compound Imaging for 2D Motion Vector Estimation: Application to Transient Elastography", Ultrason. Ferroelectr. Freq. Control., the lateral component of tissular speed $V_y$ can also be accessed. When using a double mechanical scan like the one represented in FIG. 2 three components of the tissular speed are accessed: Bar 6 allows $V_x$ and $V_y$ to be measured and bar 5 allows $V_y$ and $V_z$ to be measured. The accuracy of the estimation of $V_y$ is increased by calculating the half sum of the estimations with the two bars 5 and 6.

During the course of the optional step of calculating the tissular deformation speeds the tissular deformation speed is obtained by deriving $V_z$, also noted v(z, t), along the direction of the component considered, here in relation to the depth:

$$\varepsilon_i(z,t) = \frac{\partial v_i(z,t)}{\partial i}$$

with i=x, y or z

The inversion step of the data comprises resetting or recovering the parameters that describe the viscoelastic environment. If the linear and isotropic environment is considered, these parameters are two in number. Shearing module μ and compression module λ can be selected. In practice, in the soft tissues λ is on the order of the Gpa and varies very little. μ is on the order of the Kpa. The elasticity or Young module is equal in a first approximation to 3μ. Thus, it is appropriate to determine shearing module μ that constitutes the most significant parameter of the viscoelastic environment measured.

In the case of a simple mechanical scanning, that is to say, comprising one unidirectional bar 1, all the components of the tissular speed vector are not known. The data can be inverted using the following equation:

$$\rho \frac{\partial^2 v_i}{\partial t^2} = \mu(x,y,z)\left[\frac{\partial^2 v_i}{\partial x^2} + \frac{\partial^2 v_i}{\partial y^2} + \frac{\partial^2 v_i}{\partial z^2}\right]$$

in which i=x, y or z.

In order to pose the above equation, it was necessary to make the hypothesis that the elastic waves traversing the environment are purely shearing waves. In practice, this hypothesis is false because the tissues are not perfectly non-compressible, which has the consequence that a shearing wave is necessarily accompanied by a compression wave.

The parameter sought, μ(x,y,z), is obtained by discretizing this equation. In elastography, one of the three coordinates $v_x$, $v_y$ or $v_z$ is generally available. Assume that it is $v_x$. In order to discretize this equation it is necessary to be able to calculate the second derivatives in the three directions and in time:

$$\begin{cases} \frac{\partial^2 v}{\partial x^2} \approx \frac{V(j,k+1,l,m) + V(j,k-1,l,m) - 2V(j,k,l,m)}{\Delta x^2} \\ \frac{\partial^2 v}{\partial y^2} \approx \frac{V(j,k,l+1,m) + V(j,k,l-1,m) - 2V(j,k,l,m)}{\Delta y^2} \\ \frac{\partial^2 v}{\partial z^2} \approx \frac{V(j,k,l,m+1) + V(j,k,l,m-1) - 2V(j,k,l,m)}{\Delta z^2} \\ \frac{\partial^2 v}{\partial t^2} \approx \frac{V(j+1,k,l,m) + V(j-1,k-1,l,m) - 2V(j,k,l,m)}{T^2} \end{cases}$$

in which V(j,k,l,m)=v(jT, k.Δx, y=1.Δy, m.Δz).

It is therefore not only necessary to know the displacement vx in the image plane but also to know it around the image plane to be able to estimate the second derivative perpendicular to the image plane: $\delta v^2/\delta z^2$. In French Patent Application Publication No. FR 2 791 136 and the publications in impulsive elastography the second derivative perpendicular to the image plane is eliminated from the equation because it can not be measured experimentally. In fact, v is only measured in the (x,y) plane, only v(x,y) is known. $\delta v^2/\delta z^2$ cannot be determined. A known hypothesis consists in posing:

$$\frac{\partial^2 v}{\partial z^2} = 0$$

The equation is simplified to $$\rho \frac{\partial^2 v_i}{\partial t^2} = \mu\left[\frac{\partial^2 v_i}{\partial x^2} + \frac{\partial^2 v_i}{\partial y^2}\right]$$

in which i=x, y or z.

It can be resolved without knowing the displacements in the plane located on both sides of the image plane in z+Δz and z−Δz.

The hypothesis of nullity of the second derivative perpendicular to the image plane is particularly constraining and does not allow the resolution of the inverse problem under good conditions since it is highly improbable that $\delta v^2/\epsilon z^2$ is zero. The lacking derivative can be obtained by the device of the invention.

Thus, two solutions are envisaged for measuring v(x, y, z) and calculating $\delta v^2/\delta z^2$:

either a 1.5 D bar is used or a wye transducer allowing a focalization at three different points of elevation, or the acquisition is reproduced three times by successively shifting the bar in z−Δz, z and z+Δz with Δz judiciously selected in such a manner as to be close to the resolutions obtained at x and y (Δz≡Δx and Δy).

Figure 5:
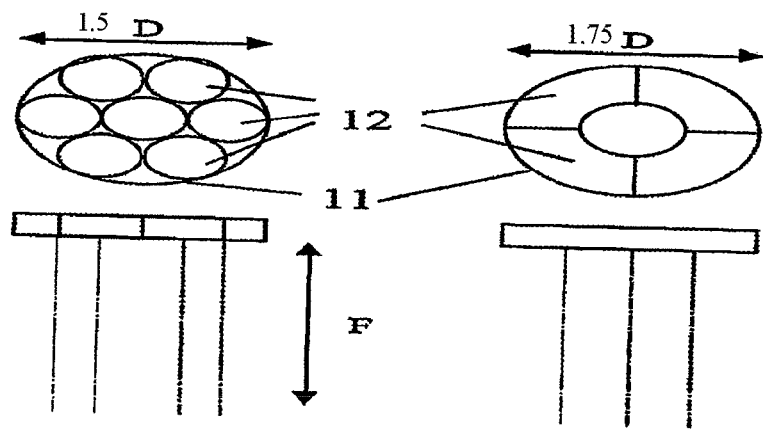
FIG. 5 is a front elevational view showing the device of the invention provided with a wye transducer in which the transducers are spatially distributed.

If a bar which is a 1.5 D bar or a 1.75 D bar is used, images 10 can be realized in three planes of the image and the displacements can be calculated in these three planes located, e.g., at z−Δz, z and z+Δz. The maximum cadence is nevertheless reduced here by a factor of 3. It is likewise possible to use a wye transducer 11 in which transducers 12 are distributed spatially, as shown in FIG. 5.

In the second solution, comprising reproducing the acquisition three times and successively shifting the bar at z−Δz, z and z+Δz, it should be noted that it is necessary that the viscoelastic environment to be measured did not move between two acquisitions and that the applied low-frequency applied force is synchronized for each position in elevation.

In the case of a double mechanical scan, that is, one comprising either two bars 5, 6 or one bar moving along two axes, all the components of the tissular speed vector are known. A more general case (compressible environment) comprises using the Navier equation, that is written:

$$\rho \frac{\partial^2 \vec{v}}{\partial t^2} = (\lambda + \mu) \vec{\nabla}(\vec{\nabla} \cdot \vec{v}) + \mu \vec{\nabla}^2 \vec{v}$$

This result can be fine-tuned with the following equation:

$$\rho \frac{\partial^2 \vec{v}}{\partial t^2} = \frac{\partial}{\partial x_i}\left[\lambda \frac{\partial v_j}{\partial x_j}\right] + \frac{\partial}{\partial x_j}\left[\mu\left(\frac{\partial v_i}{\partial x_j} + \frac{\partial v_j}{\partial x_i}\right)\right]$$

in which $v_1 = v_x$, $v_2 = v_y$, $v_3 = v_z$, $x_1 = x$, $x_2 = y$ and $x_3 = z$.

There is then a system of three equations and two unknowns: $\lambda(x,y,z)$ and $\mu(x,y,z)$ because the density $\rho$ varies very little in the tissues.

It can be understood with the above equation why neglecting the tissular speeds linked to the compression waves is a source of error. To be sure, the tissular speeds linked to the compression waves are low compared to those generated by the shearing wave. However, their contribution can not be neglected because the coefficient $\lambda$ in factor is great in front of the compression term. The discretization of this equation can be realized if the three components of the tissular speed vector are known. In fact, this equation causes couplings to intervene between the evolutions of the tissular speeds in all directions.

Figure 6:
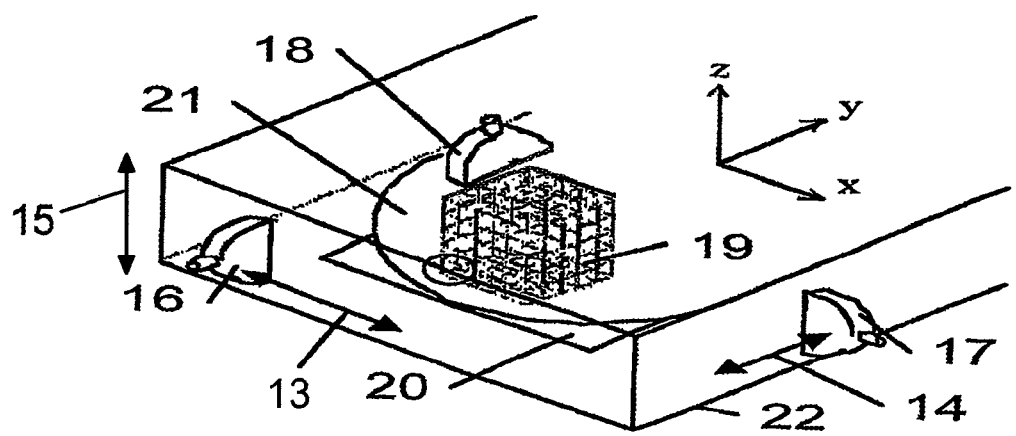
FIG. 6 is a schematic diagram showing the device of the invention measuring the elasticity of the breast of a patient.

The invention uses a mounting or device such as is shown in FIG. 6. This device permits the measuring of the three components of the tissular speed vector in the organ studied while successively scanning the environment along three different axes 13, 14 and 15. Bar 16 allows the measuring of the tissular along direction y noted $u_y$, bar 17 for measuring $u_x$, and bar 18 for measuring $u_z$. The use of an algorithm for measuring transverse displacements can allow the number of scanning zones to be reduced from three to two by eliminating, e.g., bar 18. Displacement $u_z$ would then be determined simultaneously with bar 16 and bar 17, which would allow an average $u_z = (u_{zB1} + u_{zB2})/2$ to be made.

A system of synchronization allows transducer 12 to be shifted between two acquisitions, one acquisition comprising the generation of elastic shearing waves and the acquisition of the ultrasonic signals. The displacement of the system can be realized, e.g., with a motor step-by-step or an electrodynamic actuator.

This acquisition sequence should be reproduced as many times as there is a plane in the image. When using three bars 16, 17, 18, each one taking 128 different positions, the system requires 384 distinct acquisition sequences. The environment studied can then be segmented into $128^3$ voxels 19 with a cubic shape. The acquisition cadence of the ultrasonic signals is between 100 and 100,000 shots per second.

Suppose that the shearing waves propagate at 1 m/s in the environment studied and that the main dimension of this environment is 12/8 cm and that the voxels have 1 mm$^3$ for dimension. The propagation of the shearing wave in such an environment and with a length of 12/8 cm lasts 128 ms. For a typical cadence of 1,000 shots per second, 128 ultrasonic shots should be realized to follow the propagation of the shearing wave. It can then be estimated that at the end of 150 ms the acquisition is concluded. Suppose that the ultrasonic device shifts at the end of 500 ms and that a second series of 128 ultrasonic shots is realized. If three ultrasonic bars are used for acceding to the three components of the displacement, approximately 3 minutes will be required (384 times 500 ms) to acquire all the data necessary for the resolution of the inverse problem. This measuring time can be reduced by interlacing the ultrasonic shots, and 128 shots would then be necessary for one minute of acquisition.

In the case of scanning, one of the difficulties comprises maintaining a good coupling between the transducer and the environment studied during the entire duration of the scan. In the case in which the surface of the environment is planar the scanning can be realized using an ultrasonic coupler, e.g., a water-based gel. When this is not possible or when the surface of the environment is "uneven", the viscoelastic environment is immersed in water. This is represented in FIG. 6 in which the breast 21 of the patient is immersed in parallele-pipedic reservoir 22 comprising windows transparent to the ultrasounds and filled with water.

As we have seen above, the device of the invention requires at least one echographic bar. It also requires electronic equipment for ultrasonic acquisition constituted of ultrasonic transmitters and receivers, digital-to-analog and analog-to digital converters, memories, digital and analog transmission lines, etc. In general, a processing unit that can be, e.g., a PC computer associated with a user interface is added to this electronic equipment dedicated to the digitization of the ultrasonic signals. The elements mentioned in this paragraph are not represented in the various figures but are perfectly known to the expert in the art.

The ultrarapid, ultrasonic imaging techniques generally use only a limited number of ultrasonic emissions to illuminate the entire environment to be imaged. They therefore have the disadvantage of sending less energy into the environment than a standard echographic system. Consequently, the signal-to-jamming ratio to noise falls and the dynamics of the ultrasonic image diminishes, which entails a degradation of the raw ultrasonic data and is reflected in the chain of algorithms, degrading the measures of elasticity in terms of sensitivity, resolution, etc.

In order to alleviate this disadvantage, the device of the invention brings a part of the above-mentioned electronic equipment into the proximity, that is, typically a distance less than 50 centimeters, of the ultrasonic bar with the following consequences:

An increase in the sensitivity of the system,

An increase in the energy transmitted,

A simplification of the connections between the motorized sensor part (bar+brought-up electronic equipment) and the data processing unit (PC or brought-up PC card or DSP processor, etc.), A greater immunity to noise.

These modifications bring about a reduction of the mobility of the bar that would not be compatible with a standard use in echography because echographic bars should be light and manageable. It is important to note that the mobility of the bar is in any case limited by the course of the scan. The weight of the bar is less important because the bar is not manipulated. It is motorized.

According to one aspect of the invention the device places the analog part of emission and of reception, that is to say, the amplifiers of emission and of reception, in the proximity, that is typically less than 50 cm, of the bar while retaining a transmission of analog signals of average levels between the sensor part and the processing unit. In this manner the path of the strong (after amplification) analog emission signals and that of the weak (before amplification) reception signals are reduced, as a consequence of which the reception sensitivity is increased and the transfer of energy to the emission improved.

According another aspect of the invention the device places the analog-to-digital converters (CAN) and the digital-to-analog converters (CNA) (for the emission and the reception) in the proximity, still typically less than 50 cm, of the bar and to connect the sensor part and the processing unit by a very high-speed digital connection (of the LVDS type, for example). The structure of the device of the invention realized in this manner brings about the following improvements:

Signal-to-jamming ratio to noise is increased by locating the entire analog part at the level of the source. The strong (transmitters) and weak (receivers) analog signals are concentrated at the level of the sensor and no longer traverse the distance between the processing unit and the sensor part, the noise received and the noise emitted are reduced because the connection between the treatment unit and the sensor unit becomes purely digital, the connection between the command/treatment means and the sensor pat is simplified in terms of the number of wires.

As an example, an operator uses a bar of 128 elements and 8 bit converters (CAN and CAN) at 50 MHz for the emission and the reception. If emission and reception are separated in time and all paths are active, the transfer rate of digital data reaches 128×8×50=51.2 gbps (gigabits per second). Currently, 17 high-speed digital connections at 3.125 gbps are sufficient for transmitting this data in real time. By way of comparison, an analog solution would require 128 two-wire connections.

Figure 7:
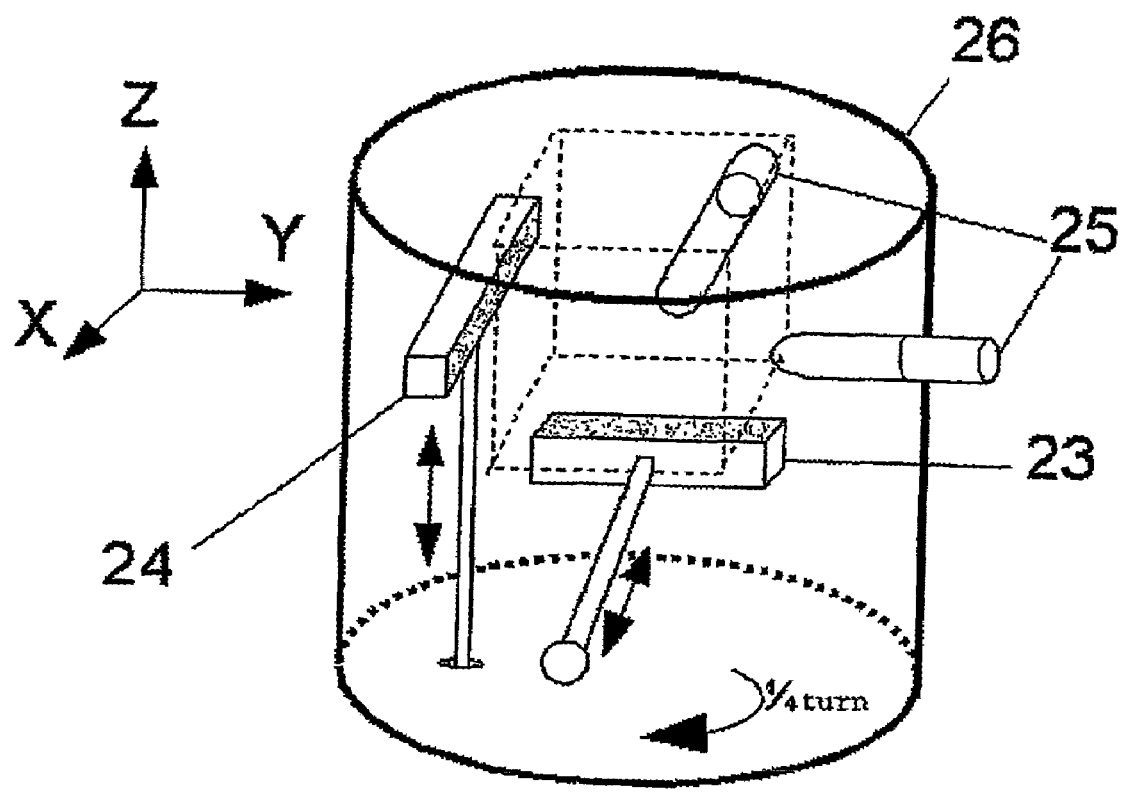
FIG. 7 is a schematic diagram showing one aspect of the device of the invention.

FIG. 7 shows the device of the invention in a new mounting. In this aspect, two ultrasonic probes 23, 24 are used and immersed in hermetic container 26 filled with water or some other suitable liquid.

The hermetic container or box is capable of rotating, e.g., a quarter turn in such a manner that probe 23 can not only scan along direction X but also along direction Z. Ultrasonic probe 24 scans solely along direction Z. The acquisition of the ultrasonic signals is therefore made in three times:

scanning along directions X and Z by two probes 23, 24, rotation of hermetic container or box 26 by, e.g., a quarter turn, that is, 90°, and scanning along direction Z by probe 23.

During the acquisitions mechanical vibrators 25 inserted in orifices present on the periphery or circumference of hermetic container 26 can be used to produce low-frequency applied forces. One of the two mechanical vibrators or both mechanical vibrators shown in FIG. 7 can be replaced by a hyperthermal probe and/or an ultrasonic transducer used in remote palpation mode. In the example selected for illustrating the invention the two orifices present in or on hermetic box 26 are located at 90° from one another, that is to say that the linear mechanical vibrators are positioned perpendicular to one another in such a manner that even after a quarter turn (90°) of container 26 the mechanical vibrators still extend along the same directions, that is, the same straight lines as previously.

The invention was described above by way of example. It is understood that different variations of the device and of the process for measuring the elasticity of a human or animal organ and a consecutive establishment of the representation of the elasticity in two or three dimensions, in particular as concerns the arranging or the managing of the different elements constituting this device or their order as well as the importance of the steps of this process are possible without departing from the scope of the invention.

The invention claimed is:

1. A device for measuring elasticity of a human or animal organ, or viscoelastic environments presenting an ultrasonic signal after ultrasonic illumination and consecutively establishing a representation in two or three dimensions of the elasticity, comprising:
    at least one echographic or ultrasonic bar comprising a plurality of transducers configured to produce a planar image;
    an excitor that generates and delivers a low-frequency, between 5 Hz and 1000 Hz, direct or indirect applied force in the form of shear waves;
    a receiver that acquires ultrasonic signals, a controller that commands and processes data;
    a scanner configured to carry out scanning with the bar in one dimension (1D) or in two dimensions (2D) in two perpendicular directions, in order to focus three different points of elevation, based on a direction perpendicular to the plane of the image, respectively, for measuring a displacement field of the shear waves along the direction perpendicular to the plane of the image; and
    a processor configured to calculate a second derivative of the displacement field in the direction perpendicular to the plane of the image, to obtain a representation of the measure of the elasticity in two (2D) or three dimensions (3D).

2. The device according to claim 1, wherein the excitor generates a mechanical vibration that can be transversal, longitudinal or a mixture of both.

3. The device according to claim 1, wherein the excitor generates a remote palpation using pressure of radiation either with the transducer(s) used for acquiring ultrasonic signals or several transducers arranged around the viscoelastic environment.

4. The device according to claim 1, wherein the excitor generates internal movements of the human or animal body.

5. The device according to claim 1, wherein the excitor comprises one or several hyperthermal transducers, either with the transducer(s) used for acquiring ultrasonic signals or one or several transducers arranged around the viscoelastic environment.

6. The device according to claim 1, wherein the ultrasonic bar is a 1.5 D bar or a wye transducer that focuses at a plurality of different points of elevation and scanning is achieved by ultrasonic focalization.

7. The device according to claim 1, wherein a space between the ultrasonic bar and the viscoelastic environment is constituted at least in part of water or any other element capable of assuring free passage of ultrasonic waves.

8. The device according to claim 2, wherein the mechanical vibration is obtained by one or several vibrating plates, piston(s) and/or bar(s).

9. The device according to claim 1, wherein the receiver comprises ultrasonic transmitters and receivers, digital-to-analog (CNA) and analog-to digital (CAN) converters, memories and digital and analog transmission lines.

10. The device according to claim 9, wherein the ultrasonic transmitters and receivers are arranged in proximity to the ultrasonic bar at a distance less than 50 centimeters.

11. The device according to claim 9, wherein the digital-to-analog converters (CNA) and the analog-to-digital converters (CAN) are situated in proximity to the ultrasonic bar at a distance less than 50 centimeters.

12. The device according to claim 11, wherein the unit constituted of the ultrasonic transducers and their on-board electronic components is connected to the controller by a very high-speed digital connection.

13. The device according to claim 1, comprising two ultrasonic bars.

14. The device according to claim 1, comprising three bars suitable for measuring tissular speeds along directions y, x and z.

15. The device according to claim 13, wherein the two bars are immersed in a hermetic container filled with a liquid.

16. The device according to claim 15, wherein the hermetic container is connected to a rotator suitable for rotating the container.

17. The device according to claim 15, wherein the hermetic container comprises a plurality of orifices into which a mechanical vibrator and/or an ultrasonic transducer is/are introduced.

18. The device according to claim 15, wherein the orifices are situated at 90° (degrees) from each other or one from the other.

19. A process for measuring elasticity of a human or animal organ, or viscoelastic environments presenting an ultrasonic signal after ultrasonic illumination and consecutively establishing a representation in two or three dimensions of the elasticity, comprising:
   generating a low-frequency applied force or signal in the form of shear waves with an echographic or ultrasonic bar configured to produce a planar image;
   acquiring ultrasonic signals with the bar in three different points of elevation, based on the direction perpendicular to the plane of the image to obtain a representation of the measure of the elasticity in two dimensions (2D) or three dimensions (3D);
   generating ultrasonic images;
   calculating tissular speeds based on measuring second derivatives of the longitudinal component of the deformation speed along three orthogonal directions in space; and
   inverting the data by recovering parameters describing the viscoelastic environment.

20. The process according to claim 19, wherein the low-frequency applied force or signal has a frequency between 5 Hz and 1000 Hz.

21. The process according to claim 19, further comprising calculating tissular deformation speeds.

22. The process according to claim 19, wherein spatial derivatives of three components of the tissular speed along three directions in space are measured during calculation of the tissular speeds.

23. The process according to claim 19, wherein acquiring the ultrasonic signals takes place while emitting an impulse with an ultrasonic transducer(s) that is reflected by particles contained in the viscoelastic environment.

24. The process according to claim 19, wherein acquiring ultrasonic signals is realized at a cadence of 1/T between 100 Hz and 100,000 Hz, where T is a period between two ultrasonic emissions.

25. The process according to claim 23, wherein acquiring ultrasonic signals is realized at a cadence of 1/T between 100 Hz and 100,000 Hz, where T is a period between two ultrasonic emissions.

26. The process according to claim 19, wherein displacement of the bar is realized by mechanical scanning or an ultrasonic scanning in elevation.

27. The device of claim 1, wherein the scanner focuses three different points of elevation using a process selected from the group consisting of:
   a mechanical displacement of the echographic or ultrasonic bar, according to a direction perpendicular to the plane of the image,
   a mechanical displacement of two echographic or ultrasonic bars, each displaced, and
   an electronic modification of the laws of focalization of the echographic or ultrasonic bar.

28. The process of claim 19, further comprising focusing the three different points of elevation using a process selected from the group consisting of:
   mechanically displacing the echographic or ultrasonic bar, according to a direction perpendicular to the plane of the image,
   mechanically displacing two echographic or ultrasonic bars, each displaced, and
   electronically modifying the laws of focalization of the echographic or ultrasonic bar.

* * * * *